United States Patent [19]

Bernhard et al.

[11] Patent Number: 5,738,647
[45] Date of Patent: Apr. 14, 1998

[54] USER ACTIVATED IONTOPHORETIC DEVICE AND METHOD FOR ACTIVATING SAME

[75] Inventors: Michael I. Bernhard, Summit, N.J.; John D. DeNuzzio, Chapel Hill, N.C.

[73] Assignee: Becton Dickinson and Company, Franklin Lakes, N.J.

[21] Appl. No.: 722,813

[22] Filed: Sep. 27, 1996

[51] Int. Cl.⁶ ....................................... A61N 1/30
[52] U.S. Cl. ............................... 604/20; 607/153
[58] Field of Search ................... 604/20, 21; 607/153

[56] References Cited

U.S. PATENT DOCUMENTS

| | | |
|---|---|---|
| 4,911,707 | 3/1990 | Heiber et al. . |
| 4,917,676 | 4/1990 | Heiber et al. . |
| 5,128,137 | 7/1992 | Müller et al. . |
| 5,310,404 | 5/1994 | Gyory et al. ............................... 604/20 |
| 5,445,609 | 8/1995 | Latter et al. ............................... 604/20 |
| 5,662,925 | 9/1997 | Ebert et al. . |

Primary Examiner—Mark Bockelman
Assistant Examiner—Ellen S. Tao
Attorney, Agent, or Firm—Allen W. Wark

[57] ABSTRACT

A user activated iontophoretic device of the present invention includes an electrode assembly, an electrode reservoir and at least one drug reservoir. The device is divided or otherwise separated into at least two portions, with one portion containing the electrode reservoir and the other containing the drug reservoir, which may include a medication in a dry form. The electrode reservoir and the drug reservoir are sealingly separated by a barrier, which can be removed to bring the reservoirs into fluid conducting contact with one another. A method of activating the device includes causing the two portions to come into fluid conducting contact with one another to at least partially hydrate one of the reservoirs. This can be accomplished by removing the barrier dividing the two portions. In this way, the device is suitable for use to deliver a drug which has limited stability in an aqueous solution.

18 Claims, 8 Drawing Sheets

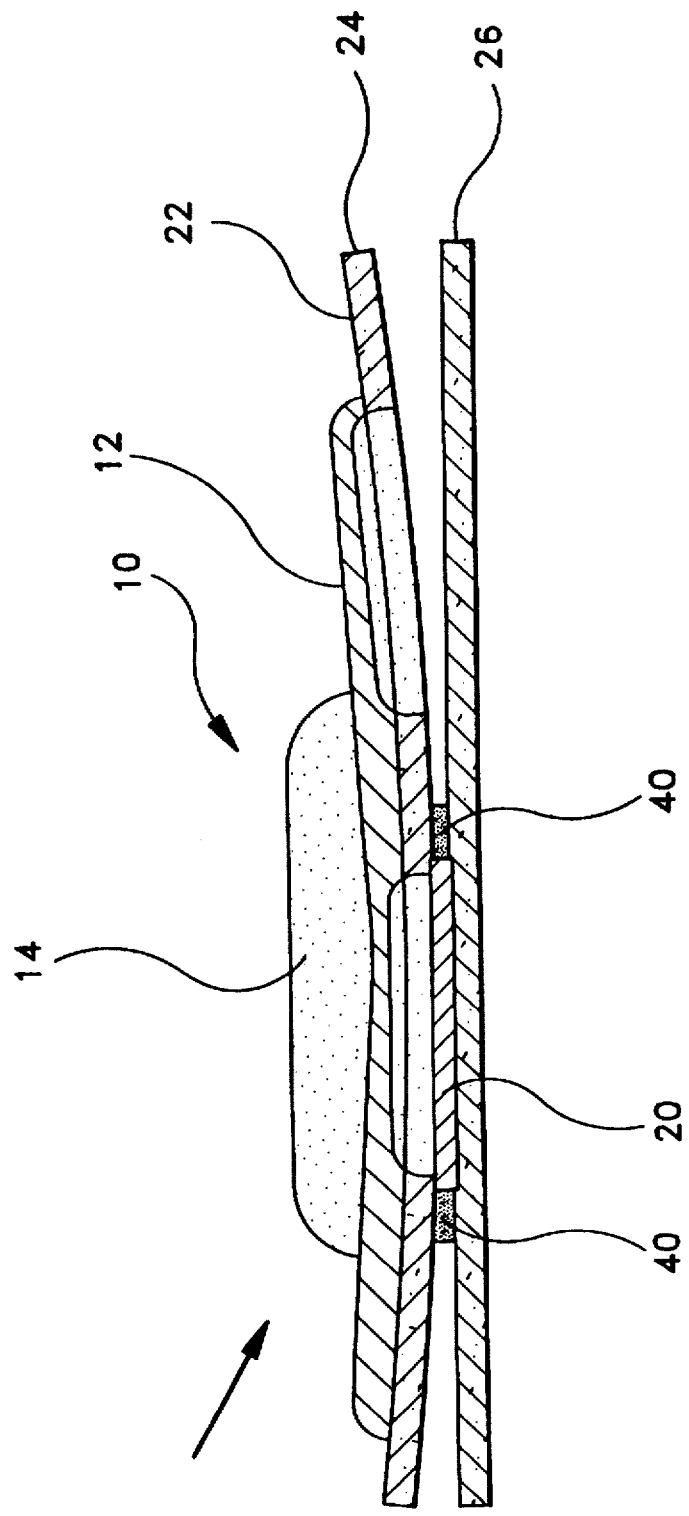

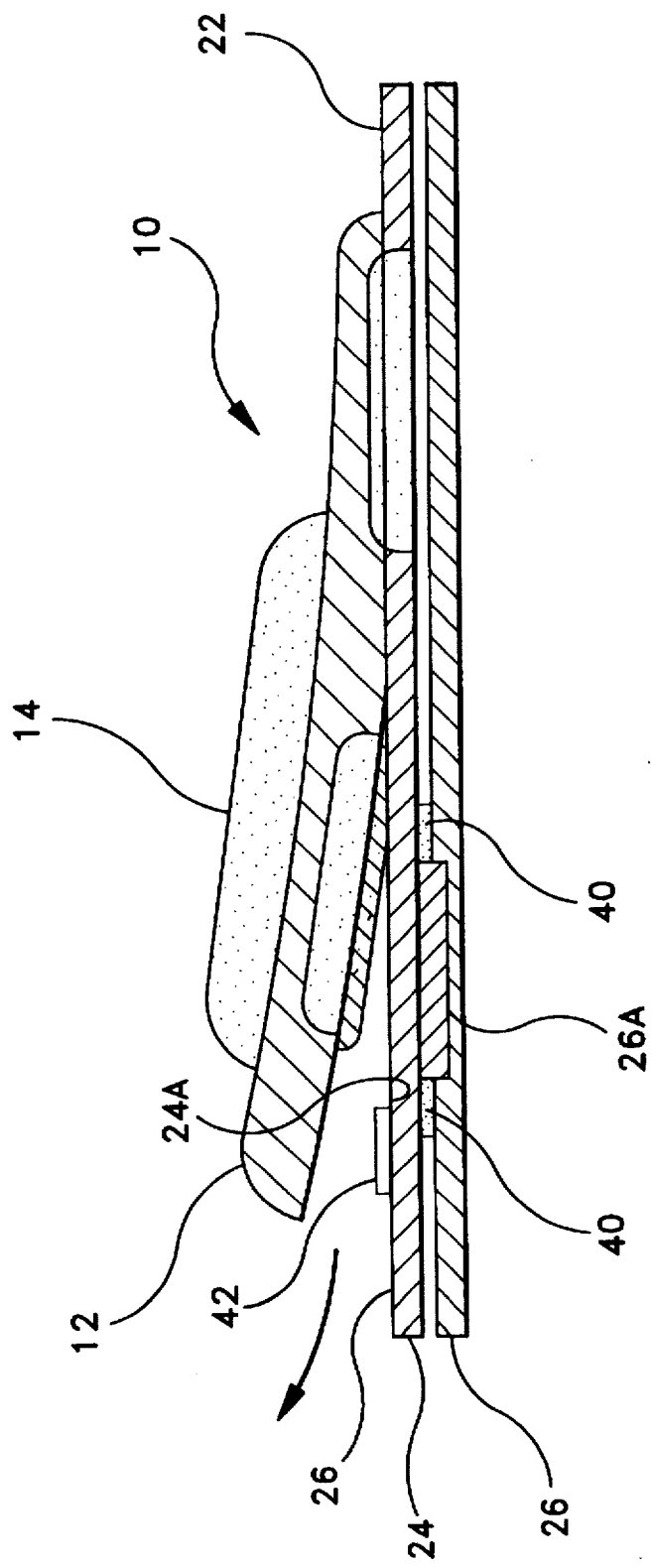

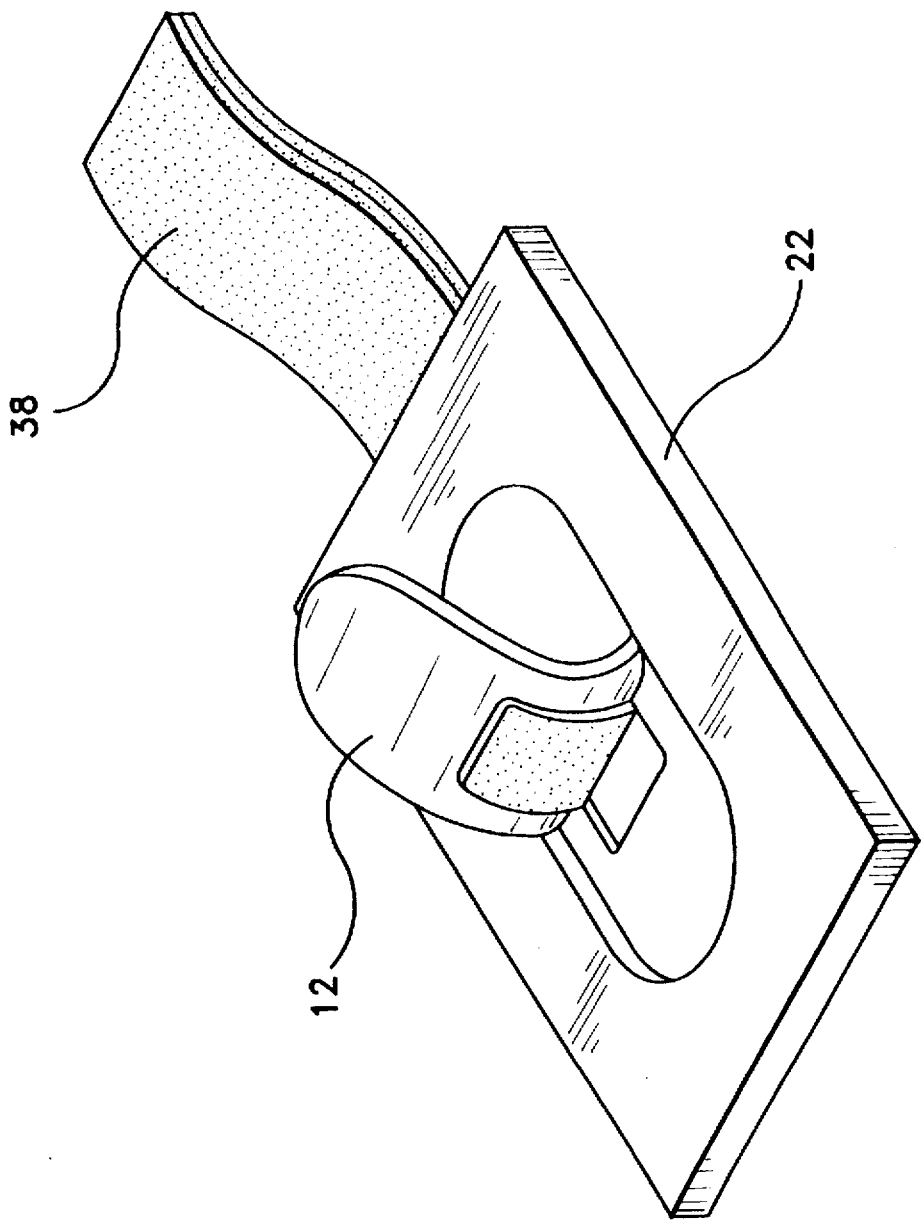

USER ACTIVATED IONTOPHORETIC DEVICE AND METHOD FOR ACTIVATING SAME

FIELD OF THE INVENTION

The present invention generally relates to iontophoretic drug delivery systems for delivering drugs, medicines, medicaments and the like to patients transdermally, i.e., through the skin, and more specifically relates to an iontophoretic device and method capable of being activated by the user.

BACKGROUND OF THE INVENTION

Transdermal drug delivery systems have, in recent years, become an increasingly important means of administering drugs and like therapeutic agents.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using, for example, iontophoresis, which according to Stedman's Medical Dictionary, is defined as "the introduction into the tissues, by means of an electric current, of the ions of a chosen medicament." Such systems offer advantages clearly not achievable by any other methods of administration, such as avoiding introduction of the drug through the gastrointestinal tract or punctures in the skin to name a few.

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes, which are in contact with a portion of a patient's body. A first electrode, generally called the active electrode, delivers the ionic substance or drug into the body by iontophoresis. The second electrode, generally called the counter electrode, closes an electrical circuit that includes the first electrode and the patient's body. Generally, the circuit includes a source of electrical energy, such as a battery. The ionic substance to be driven into the body may be either positively charged or negatively charged. In the case of a positively charged ionic substance, the anode of the iontophoretic device becomes the active electrode and the cathode serves as the counter electrode to complete the circuit. Alternatively, if the ionic substance to be iontophoretically delivered is negatively charged, the cathode will be the active electrode and the anode will be the counter electrode.

In practice, this process is typically achieved by placing the ionic drug either in solution or in gel form on a carrier and placing the drug-containing carrier, for example, in the form of a drug-filled adhesive patch, into contact with the skin. The pair of electrodes is placed in contact with the skin and with the carrier. Current is applied between the two electrodes. Under the influence of the electric field present, the drug molecules migrate through the skin. As current flows between the two electrodes placed at spaced apart locations on the skin, the current path carries the drug with it.

However, with the increasing use of drugs, particularly peptides, peptidomimetics and the like, several disadvantages and limitations have been associated with the use of such devices for delivering such drugs, including storage stability as a result of the drug not being in a form suitable to provide a commercially practical shelf life because of limited stability in an aqueous solution. Upon storage for extended periods, the therapeutic agents can degrade and become less potent. In additions such devices have not delivered an efficient dosage of the drug resulting in poor performance and a need for larger amounts of the drug, which upon completion of the application is wasted. Accordingly, such devices have been generally impractical for use on outpatients and in doctor's offices, since the products do not have sufficient shelf life and neither the patient nor the practitioner wishes to wait the required time for the desired effect.

Several of the prior systems have attempted to overcome or minimize such limitations by adding the drug to the device prior to use or by maintaining the drug and/or electrode in a dry state prior to activation as disclosed, for example, in U.S. Pat. Nos. 4,722,726 (Sanderson et al.), 4,842,577 (Konno et al.), 4,911,707 (Heiber et al.), 4,917,676 (Heiber et al.), 5,087,242 (Pentelenz et al.), 5,158,537 (Haak et al.), 5,310,404 (Gyory et al.), and 5,385,543 (Haak et al.), the disclosures of which are hereby incorporated by reference in their entirety. However, limitations remain with respect to the use of such devices, particularly ease of activation. Also, slow transport and equalization between the compartments can dilute the drug formulation, thus decreasing the dose efficiency of the device.

Thus, there has been a need for a user activated iontophoretic devices which would eliminate the problems and limitations associated with the prior devices discussed above, most significant of the problems being associated with ease of use to activate the device.

SUMMARY OF THE INVENTION

In contrast to the prior devices discussed above, it has been found that an iontophoretic device particularly suited for use to deliver drugs having limited stability in an aqueous environment, while being easily activated by the user to administer the drug, can be constructed in accordance with the present invention. Such users may include the patient as well as doctors, nurses and the like.

The user activated iontophoretic device of the present invention for use in delivering at least one medication through an applied area of a patient, such as the skin, mucus membrane and the like, includes a first portion and a second portion, the first portion including an electrode assembly and a electrode reservoir and the second portion including a drug reservoir. The electrode assembly includes electrode means for driving a medication into the patient to be absorbed by the body of the patient, and the drug reservoir containing a active compound to be delivered to the applied area of the patient. The device also includes barrier means for sealingly separating the first portion and the second portion separate from one another, with the electrode assembly maintained in electrically communicating relation with the electrode reservoir, and with the active compound contained by the drug reservoir maintained separate in relation to the first portion prior to activation so that upon removal of the barrier means, the electrode reservoir and the drug reservoir are brought into fluid conducting contact with one another so that the drug is dissolved in an aqueous solution contained in the electrode reservoir.

In the preferred embodiment of the user activated iontophoretic device, upon activation, the active compound may be dissolved at an interface of the two reservoirs. Also, the active compound is initially in a dry form, separated from the electrode reservoir with the barrier means sealing the electrode reservoir in the first portion and sealing the drug reservoir contained in the second portion. In addition, the active compound in a dry form is homogeneously distributed in a carrier material so that the active compound may be kept in a dry form, separated from the electrode reservoir with the barrier means maintaining an aqueous solution in the electrode reservoir intact during storage. The active compound may be selected from the group including cell adhesion molecules, GPIIb/IIIa receptor antagonists for the treatment of various thromboembolic disorders. The electrode reservoir includes an electrolyte such as an electrically conductive gel. The barrier means includes an upper release member and a lower release member so that manipulation of the barrier means brings the electrode reservoir and the drug reservoir into fluid conducting contact with one another, with the upper release member and the lower release member interconnected by a pull tab member extending from the first portion and the second portion so that upon pulling the tab member to at least partially remove the barrier from therebetween, the electrode reservoir and the drug reservoir are brought into contact with one another. Further, the first portion includes a compartment for at least containing the electrode reservoir and the second portion includes a compartment for containing the drug reservoir with the compartments separated by the barrier means so that the active compound is otherwise isolated from the electrode reservoir and the device may be activated by removing the barrier means to bring the electrode reservoir and the drug reservoir into fluid conducting contact with one another.

The method of the present invention for iontophoretically delivering at least one medication through an applied area of a patient such as the skin, mucus membrane or the like, includes the steps of exposing a first portion of a device including an electrode assembly and an electrode reservoir by manipulating a first release member, exposing a second portion of the device including a drug reservoir containing an active compound to be delivered to the patient by manipulating a second release member, bringing the electrode reservoir of the first portion of the device into fluid conducting contact with the drug reservoir of the second portion of the device to at least partially hydrate one of the reservoirs and to form a combined reservoir, with the combined of the device to be applied to an area of the patient to be treated, and causing current to flow through the device into the applied area to drive the medication into the body of the patient.

In the preferred embodiment of the method, the step of bringing the two portions into contact with one another includes pulling a tab member to simultaneously remove the upper and lower release members from the device separating the first portion from the second portion to bring the electrode reservoir and the drug reservoir into contact with one another. Also, the method also includes the step of removing a patch from the first portion for application to the skin of the patient. In addition, the step of bring the electrode reservoir and the drug reservoir into contact with one another includes hydrating the drug reservoir or dissolving the drug contained in the drug reservoir into the electrode reservoir.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIG. 3 is a schematic, cross-sectional side view of the patch interconnected with a controller and attached to the supporting structure;

FIG. 4 is a schematic, cross-sectional side view of the patch and controller being removed from the supporting structure for attachment to the skin of a patient; and FIGS. 5A, 5B, 5C and 5D are schematic, perspective views of the iontophoretic system, including the patch and controller, being activated for attachment to the skin of a patient.

DETAILED DESCRIPTION OF THE PREFERRED EMBODIMENT

Figure 1:
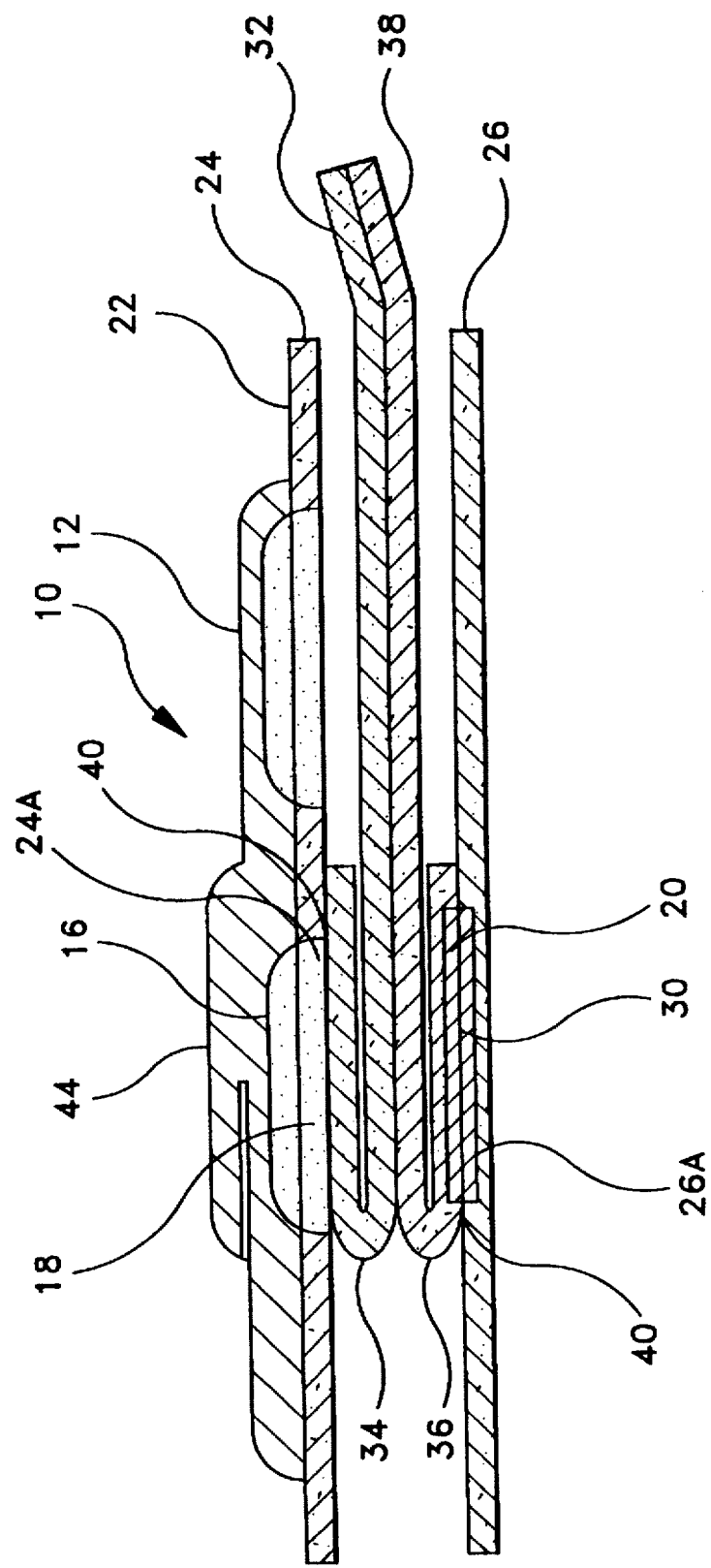
FIG. 1 is a schematic, cross-sectional side view of the patch of the present invention.

The user activated iontophoretic system of the present invention is illustrated in FIGS. 1–5 and generally includes the designation 10. Referring to FIGS. 1–4, and in particular FIGS. 3 and 4, the device or system 10 of the present invention includes a patch 12 and a controller 14, (see FIGS. 3 and 4) which in the preferred embodiment is reusable and releasably attachable to the patch (See FIGS. 1 and 2).

In the preferred embodiment illustrated in FIGS. 1–4, the patch 12 includes an electrode assembly 16, having at least one electrode, an electrode reservoir 18 and at least one drug reservoir 20, which are held together by a suitable supporting structure 22. Preferably, the electrode is adhered to the electrode reservoir. It should be appreciated that a return electrode may be combined in the electrode assembly 16 or separately provided as is well known in the art and disclosed for example, in application Ser. No. 08/541,058, pending, entitled "IONTOPHORETIC DRUG DELIVERY SYSTEM AND METHOD FOR USING SAME" and U.S. Pat. No. 5,540,669, the disclosures of which are hereby incorporated by reference in their entirety.

The supporting structure 22 is divided or otherwise separated into two portions 24, 26, one portion 24 (first) includes a compartment 24A for at least containing or otherwise accommodating the electrode assembly 16 and the electrode reservoir 18 with the electrode reservoir being situated adjacent to the electrode assembly and holding an electrolyte. The other portion 26 (second) includes a compartment 26A for at least containing or otherwise accommodating the drug reservoir 20 which holds the medication or drug 30, preferably in an ionized or ionizable form, to be delivered iontophoretically. The particular electrolyte is not essential to the present invention and is merely a matter of choice. However, in this embodiment the electrolyte may include sodium chloride in an aqueous solution or an aqueous swollen cross-linked water soluble polymer as disclosed for example, in application Ser. No. 08/533,979, pending, entitled "IONTOPHORETIC DRUG DELIVERY DEVICE AND RESERVOIR AND METHOD OF MAKING SAME," the disclosure of which is hereby incorporated by reference in its entirety.

Figure 2:
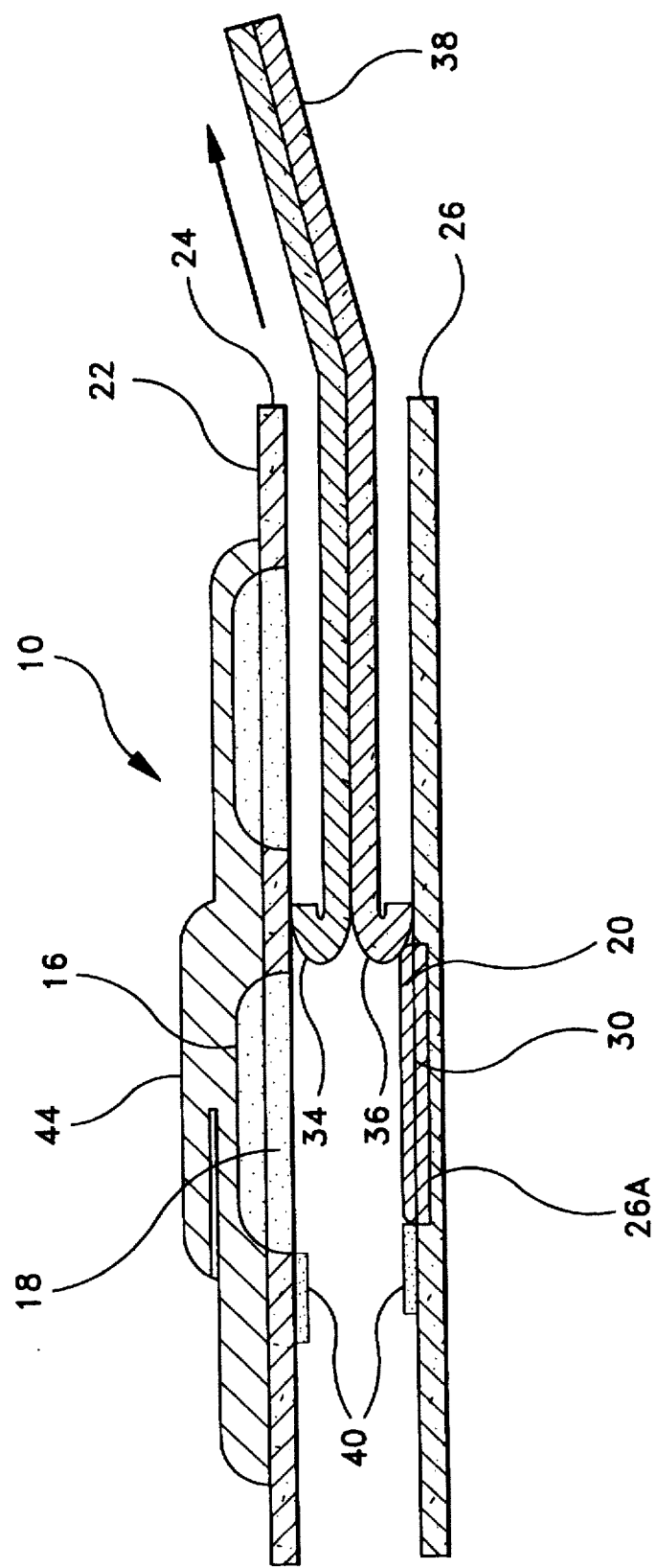
FIG. 2 is a schematic, cross-sectional side view of the patch shown in FIG. 1, with the barrier being manipulated.

Referring to FIGS. 1 and 2, the two portions 24 and 26 are separated by a barrier 32. The barrier 32 includes an upper release member 34 and a lower release member 36 connected to one another by a pull tab member 38 extending from the structure 22. In the preferred embodiment, the release members 34, 36 are both folded about their adjacent compartments. The release surfaces are provided to prevent the barrier from adhering to the adjacent portions of the reservoirs 18, 20 and to seal the peripheral area surrounding each reservoir 18,20. In this way, the drug 30 contained in the drug reservoir 20 can be stored or otherwise sealingly isolated from the electrode reservoir 18 in the first portion 24, in a dry state or formulation in a matrix or on a supporting substrate for hydration prior to use. Also, the drug can be stored in a non-aqueous solvent such as low molecular weight polyethylene glycol or glycerine. The drug may be stable in such non-aqueous solvents, and the solution (with the ionized or ionizable drug) may be an adequate electrolyte depending upon the particular drug or combination of drugs. These solvents might also be used as humectants in a gel matrix.

Also, either or both the first portion 24 and the second portion 26 preferably includes a layer of adhesive 40 surrounding the electrode reservoir 18 for sealing the two portions together upon removal of the barrier 37. However, prior to applying the device to the patient, the barrier 32 is removed or otherwise manipulated by pulling the tab member 38 to at least partially remove the barrier 32, particularly the release members 34, 36 from between the first and second portions 24, 26. In the alternative, the pull tab member may simply be attached to a suitable package (not shown) so as to be manipulated upon opening the package.

Then the controller 14 is preferably attached to the patch 12 (FIG. 3), and after a sufficient period of time, the patch 12 is removed from the structure, by for example peeling it away from the upper surface of the first portion of the structure (FIG. 4). To adhere the patch 12 to the upper surface of the first portion 24, the surface may include a layer of adhesive 42 therebetween, or the gel contained in the electrode reservoir 18 may act as an adhesive, with the adhesive 42 remaining on the first portion. This layer of adhesive, may also be used to adhere the patch to the skin of the patient. Also, the way in which the controller 14 is attached to the patch 12 can preferably be utilized to provide additional force to bring the electrode reservoir 18 and the drug reservoir 20 into contract with one another. In this way, upon activation, the electrode reservoir 18 and the drug reservoir 20 are brought into contact with one another and the drug may be dissolved at the interface of the reservoirs, due to its solubility in an aqueous fluid and/or the drug reservoir 18 is hydrated and adhered to the interface of the electrode reservoir.

As illustrated in FIGS. 3 and 4, the patch 12 is preferably releasably attached to the controller 14 by attaching or snapping the controller into the fastener 44. The particular controller is not essential to the present invention, and may include, for example, those disclosed in patent application Ser. Nos. 08/315,532, now abandoned, entitled "IONTOPHORESIS PATCH/CONTROLLER INTERCONNECTION USING A CONDUCTIVE ELASTOMER TO PROVIDE NOISE-FREE ELECTRICAL CONTACT BETWEEN PATCH AND CONTROLLER," 08/315,533, pending, entitled "IONTOPHORESIS ASSEMBLY INCLUDING CLEANABLE ELECTRICAL CONTACTS," 08/315,372, now U.S. Pat. No. 5,645,526, entitled "APPARATUS AND METHOD FOR ENSURING COMPATIBILITY OF A REUSABLE IONTOPHORETIC CONTROLLER WITH AN IONTOPHORETIC PATCH," and Ser. No. 08/534,897, now abandoned, entitled "IONTOPHORETIC DRUG DELIVERY SYSTEM, INCLUDING REUSABLE DEVICE," and U.S. Pat. No. 5,498,235 (Flower), the disclosures of which are hereby incorporated by reference in their entirety. It should be appreciated that the particular means for releasably attaching the controller 14 to the patch 12 is not essential to the present invention and is simply a matter of choice.

As is well known within the field, the device can be attached to a suitable area of the skin of the patient, with the drug containing patch in electrical conducting contact with the skin, and a voltage impressed across the electrodes of the electrode assembly 16 to cause current to flow through the skin of the patient to drive the drug into the skin and the tissue to be absorbed by the body of the patient for the desired period of time. It should also be appreciated that the device of the present invention can be applied to other areas of the body such as mucus membranes depending upon the desired therapy and drug to be delivered.

In addition, it should be appreciated that other forms of barriers may be used as long as they separate the two reservoirs 18, 20 of the two portions prior to application to prevent degradation of the drug through, for example, slow transport or equilibration between the reservoirs, or through other action which would otherwise result in the drug formulation being diluted or dissolved in an aqueous solution, thus decreasing the dose efficiency of the device, while permitting electrical conducting contact between the reservoirs after activation. In this embodiment, the barrier is a vapor/liquid impermeable barrier which may be manipulated by being removed or at least moved to activate the device.

In the preferred embodiment, the drug can be kept in a dry form (active compound), sealingly separated from the electrode reservoir 18, to keep the aqueous solution intact during storage and where the drug is kept in a dry form, separated during storage from the electrolytic solution contained in the electrode reservoir. The Drug is preferably kept in its dry form homogeneously distributed in a carrier material, e.g., cotton fiber, woven plastic thread, drug film, hydrozy methylpropylcellulose and the like, with the same surface area as the electrode reservoir 18.

Drug 30 may include cell adhesive molecules, such as by way of example and not limitation, Glycoprotein IIb/IIIa receptor antagonists (GPIIb/IIIa) and other integrin receptor antagonists, such as, GPIc/IIa, $_vB_3$ (Lefkovitz J., et al., "Platelet glycoprotein IIb/IIIa receptors in cardiovascular medicine." New Eng. J. Med. 332 (1995) 1553-9) which may be effective in the treatment of various disease states, e.g. restenosis, unstable angina, stroke, prevention of secondary myocardial infarction, etc. GPIIb/IIIa receptor antagonists bind to GPIIb/IIIa receptors on platelets to block fibrinogen binding and consequently inhibit platelet aggregation, as well as those disclosed in PCT Application No. WO 95/14683, entitled "NOVEL ISOXAZOLINE AND ISOXAZOLE FIBRINOGEN RECEPTOR ANTAGONISTS," the disclosure of which is hereby incorporated by reference in its entirety. These agents, therefore, have enormous potential for the treatment of various disorders, including thromboembolics. Also, growth hormones in dry form, i.e., cotton or woven plastic thread, impregnated with the drug in a pre-determine amount per unit length. In addition, multiple layers of the Drug or various may be used.

Thus, the present invention can be used wherein an active compound or drug needs to be isolated. However, it should also be appreciated that the electrode reservoir may contain one or more drugs which are stable in aqueous solutions and are to be co-delivered with the drug 30. Drug, medication and active compound have been used herein to mean any pharmaceutical agent, such as therapeutic compounds, diagnostic agents and the like.

Operation and Use

Having described one embodiment of the iontophoretic drug delivery system 10, including the disposable patch 12 and reusable controller 14, of the present invention, its operation and use is described below in connection with FIGS. 5A, 5B, 5C and 5D.

Figure 5A:
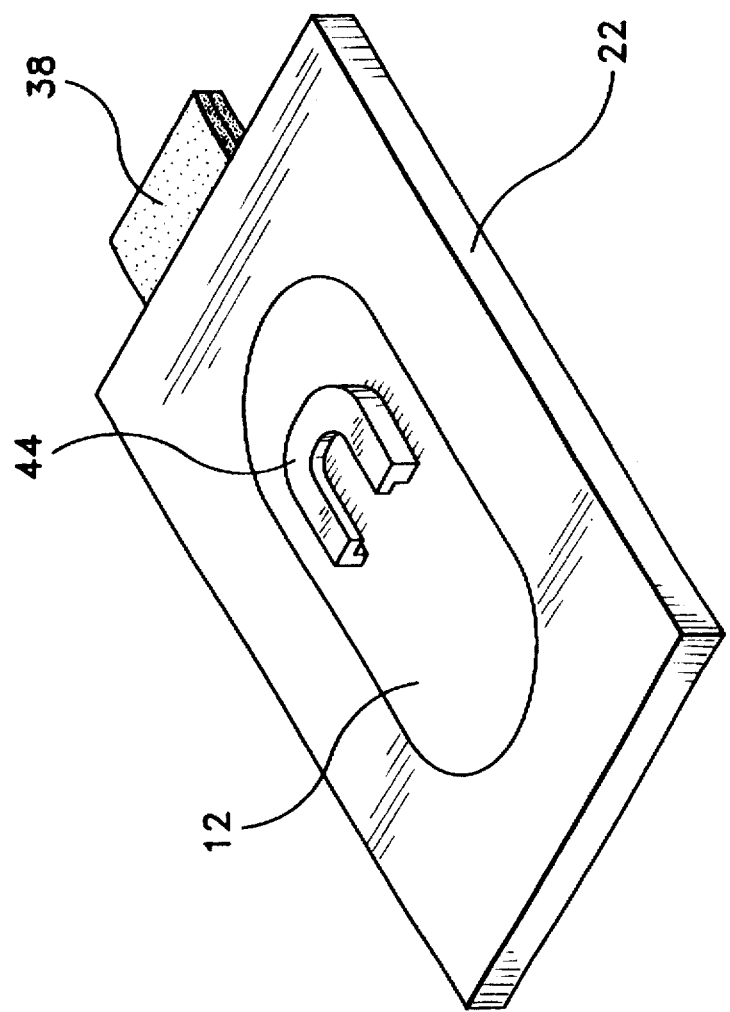
Figure 5B:
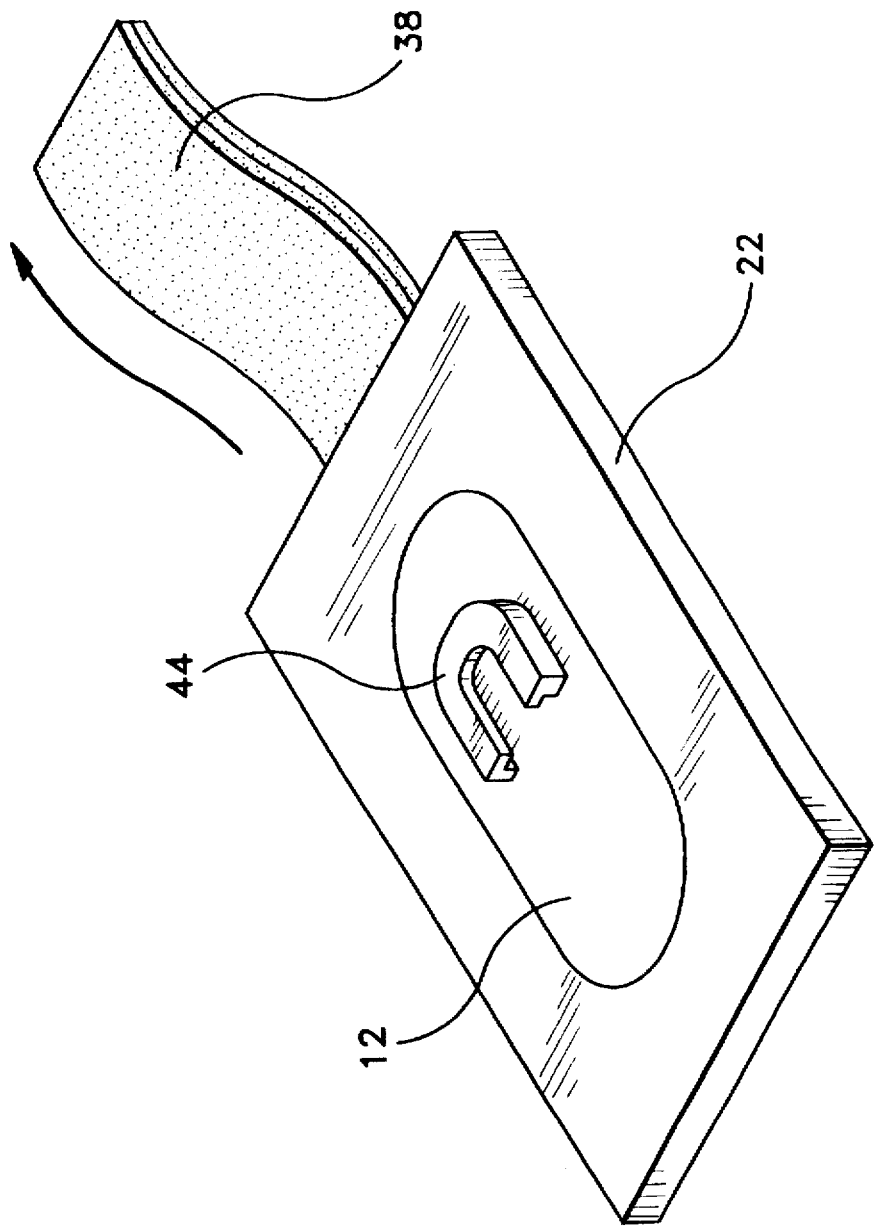
Figure 5C:
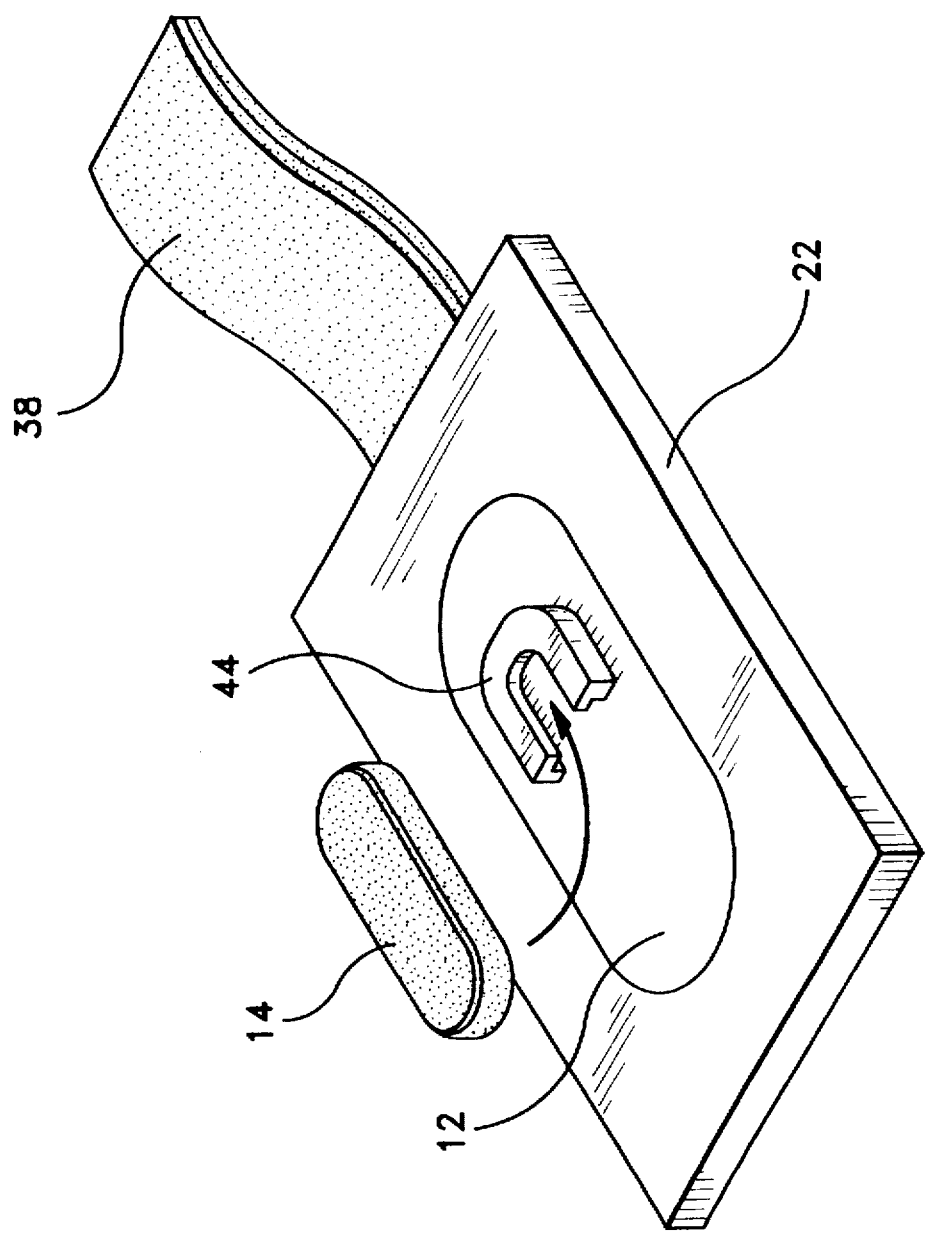

As illustrated in FIGS. 5A and 5B, initially to hydrate the drug, the pull tab member 38 is pulled from the supporting structure to expose the reservoirs. Specifically, the pulling action causes the upper release member 34 and the lower release member 36 to be drawn forward exposing the electrode reservoir 18 and the drug reservoir 20 containing the active compound to be delivered to the patient. This allows the reservoirs to be brought into contact with one another at an interface. Next, the controller 14 is fastened to the patch 10 (FIG. 5C), which may also cause the electrode reservoir into fluid conducting contact with the drug reservoir to at least partially hydrate one of the reservoirs and to form a combined reservoir portion. After waiting a sufficient period of time, such as for example a few seconds to 15 minutes, for the drug to dissolve, the combined portion of the device, including the patch 12 with the controller 14 fastened thereto, can be removed from the supporting structure 22 (FIG. 5D), and applied to an area of the patient to be treated by causing current to flow through the device into the applied area to drive the medication into the body of the patient.

Active agent, drug, formulation, medication, medicament and active compound have been used herein to mean at least one pharmaceutical agent, such as therapeutic compounds, diagnostic agents, anesthetic agents and the like.

The particular matrix of the material or the method of manufacture is not essential to the present invention. For example, the drug can be spray-dried onto an inert support such as a non-woven material, a screen or scrim, or a variety of micro-porous supports such as nylon, polyethylene, and polypropylene. In addition, the drug can be dispersed in an ointment or liquid and cast and dried onto a support. Also the drug can be mixed with dispersing agents or water-soluble polymers and pressed or evaporated into a dry wafer film or pellets that dissolve rapidly in water. The drug can be uniformly dispersed in a de-hydrated gel that can be hydrated rapidly from an added source of water.

Further, while the preferred embodiments of the present invention has been described so as to enable one skilled in the are to practice the device of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A user activated iontophoretic device for use in delivering at least one medication through an applied area of a patient, such as the skin, mucus membrane and the like, comprising:

a first portion and a second portion, said first portion including an electrode assembly and a electrode reservoir and said second portion including a drug reservoir;

said electrode assembly including electrode means for driving a medication into the patient to be absorbed by the body of the patient; and said drug reservoir containing an active compound to be delivered to the applied area of the patient, with the active compound being maintained in a dry state prior to activation of the device;

barrier means for sealingly maintaining said first portion and said second portion separate from one another, with the electrode assembly maintained in electrically communicating relation with the electrode reservoir, and with the active compound contained by the drug reservoir maintained separate in relation to the first portion prior to activation so that upon removal of said barrier means, the electrode reservoir and the drug reservoir are brought into fluid conducting contact with one another so that said drug is dissolved in an aqueous solution contained in said electrode reservoir.

2. A user activated iontophoretic device as defined in claim 1, wherein the electrode reservoir includes an electrolyte in the form of an electrically conductive gel.

3. A user activated iontophoretic device as defined in claim 1, wherein the active compound is selected from the group consisting of cell adhesion molecules, GPIIb/IIa receptor antagonists for the treatment of various thromboembolic disorders.

4. A user activated iontophoretic device as defined in claim 1, wherein said barrier means includes an upper release member and a lower release member so that manipulation of said barrier means brings the electrode reservoir and the drug reservoir into fluid conducting contact with one another.

5. A user activated iontophoretic device as defined in claim 4, wherein said upper release member and said lower release member are interconnected by a pull tab member extending from the first portion and the second portion so that upon pulling the tab member to at least partially remove the barrier from therebetween, the electrode reservoir and the drug reservoir are brought into contact with one another.

6. A user activated iontophoretic device as defined in claim 1, wherein said first portion includes a compartment for at least containing the electrode reservoir and said second portion includes a compartment for containing said drug reservoir with the compartments separated by said barrier means so that said active compound is otherwise isolated from the electrode reservoir and the device may be activated by removing said barrier means to bring the electrode reservoir and the drug reservoir into fluid conducting contact with one another.

7. A user activated iontophoretic device for use in delivering at least one medication through an applied area of a patient, such as the skin, mucus membrane and the like, comprising:

a first portion and a second portion, said first portion including an electrode assembly and a electrode reservoir and said second portion including a drug reservoir;

said electrode assembly including electrode means for driving a medication into the patient to be absorbed by the body of the patient;

said drug reservoir containing an active compound to be delivered to the applied area of the patient, said active compound is initially in a dry form;

barrier means for sealingly maintaining said first portion and said second portion separate from one another, with the electrode assembly maintained in electrically communicating relation with the electrode reservoir, and with the active compound contained by the drug reservoir separated from the electrode reservoir with the barrier means sealing said electrode reservoir in said first portion and sealing said drug reservoir contained in said second portion prior to activation so that upon removal of said barrier means, the electrode reservoir and the drug reservoir are brought into fluid conducting contact with one another so that said drug is dissolved in an aqueous solution contained in said electrode reservoir.

8. A user activated iontophoretic device for use in delivering at least one medication through an applied area of a patient, such as the skin, mucus membrane and the like, comprising:

a first portion and a second portion, said first portion including an electrode assembly and a electrode reservoir and said second portion including a drug reservoir;

said electrode assembly including electrode means for driving a medication into the patient to be absorbed by the body of the patient;

said drug reservoir containing an active compound to be delivered to the applied area of the patient, with the active compound being in a dry form and homogeneously distributed in a carrier material so that the active compound may be kept in a dry form;

barrier means for sealingly maintaining said first portion and said second portion separate from one another, with the electrode assembly maintained in electrically communicating relation with the electrode reservoir, and with the active compound contained by the drug reservoir separated from the electrode reservoir with the barrier means maintaining an aqueous solution in the electrode reservoir intact during storage prior to activation so that upon removal of said barrier means, the electrode reservoir and the drug reservoir are brought into fluid conducting contact with one another so that said drug is dissolved in said aqueous solution contained in said electrode reservoir.

9. A user activated iontophoretic device as defined in claim 8, wherein said barrier means includes an upper release member and a lower release member so that manipulation of said barrier means brings the electrode reservoir and the drug reservoir into fluid conducting contact with one another.

10. A user activated iontophoretic device as defined in claim 9, wherein said upper release member and said lower release member are interconnected by a pull tab member extending from the first portion and the second portion so that upon pulling the tab member to remove the barrier from therebetween, the electrode reservoir and the drug reservoir are brought into contact with one another.

11. A user activated iontophoretic device as defined in claim 8, wherein said first portion includes a compartment for at least containing the electrode reservoir and said second portion includes a compartment for containing said drug reservoir with the compartments separated by said barrier means so that said active compound is otherwise isolated from the electrode reservoir and the device may be activated by removing said barrier means to bring the electrode reservoir and the drug reservoir into electrical conducting contact with one another.

12. A user activated iontophoretic device as defined in claim 8, wherein the electrode reservoir includes an electrolyte in the form of an electrically conductive gel.

13. A user activated iontophoretic device as defined in claim 8, wherein the active compound is selected from the group consisting of cell adhesion molecules, GPIIb/IIIa receptor antagonists for the treatment of various thromboembolic disorders.

14. A method of iontophoretically delivering at least one medication through an applied area of a patient such as the skin, mucus membrane or the like, comprising the steps of:

exposing a first portion of a device including an electrode reservoir by manipulating a first release member;

exposing a second portion of the device including a drug reservoir containing an active compound to be delivered to the patient by manipulating a second release member;

bringing the electrode reservoir of the first portion of the device into fluid conducting contact with the drug reservoir of the second portion of the device to hydrate said drug reservoir and to form a combined reservoir, with the combined reservoir of the device to be applied to an area of the patient to be treated; and causing current to flow through the device into the applied area to drive the medication into the body of the patient.

15. A method of iontophoretically delivering at least one medication as defined in claim 14, wherein the step of bringing the two portions into contact with one another includes pulling a tab member to simultaneously remove the upper and lower release members from the device separating the first portion from the second portion to bring the electrode reservoir and the drug reservoir into contact with one another.

16. A method of iontophoretically delivering at least one medication as defined in claim 14, further comprising the step of removing a patch from said first portion for application to the skin of the patient.

17. A method of iontophoretically delivering at least one medication as defined in claim 14, wherein said step of bringing said electrode reservoir and said drug reservoir into contact with one another includes dissolving the drug contained in said drug reservoir into said electrode reservoir.

18. A method of iontophoretically delivering at least one medication as defined in claim 14, further comprising the step of removing a patch and a controller from said first portion for application to the skin of the patient.

* * * * *